(12) United States Patent
Measamer et al.

(10) Patent No.: US 8,551,058 B2
(45) Date of Patent: Oct. 8, 2013

(54) ENDOSCOPIC TRANSLUMENAL SURGICAL SYSTEMS

(75) Inventors: John P. Measamer, Cincinnati, OH (US); Michael S. Cropper, Edgewood, KY (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 520 days.

(21) Appl. No.: 11/775,477

(22) Filed: Jul. 10, 2007

(65) Prior Publication Data

US 2008/0051735 A1 Feb. 28, 2008

Related U.S. Application Data

(63) Continuation-in-part of application No. 11/382,173, filed on May 8, 2006, now abandoned.

(51) Int. Cl.
- *A61M 5/178* (2006.01)
- *A61M 5/32* (2006.01)
- *A61M 25/00* (2006.01)

(52) U.S. Cl.
USPC . 604/265; 604/158; 604/164.01; 604/167.01; 606/108

(58) Field of Classification Search
USPC .................. 600/184; 606/108; 604/164.01, 604/167.01–167.06, 278
See application file for complete search history.

(56) References Cited

U.S. PATENT DOCUMENTS

| | | | |
|---|---|---|---|
| 3,908,663 A | 9/1975 | Viek | |
| 4,230,108 A | 10/1980 | Young | |
| 4,262,677 A | 4/1981 | Bader | |
| 4,535,773 A | 8/1985 | Yoon | |
| 4,581,028 A * | 4/1986 | Fox et al. | 623/2.42 |
| 4,793,326 A | 12/1988 | Shishido | |
| 4,988,341 A * | 1/1991 | Columbus et al. | 604/306 |
| 5,059,186 A * | 10/1991 | Yamamoto et al. | 604/537 |
| 5,104,389 A * | 4/1992 | Deem et al. | 604/264 |
| 5,236,423 A | 8/1993 | Mix et al. | |
| 5,256,149 A * | 10/1993 | Banik et al. | 604/164.01 |
| 5,257,617 A | 11/1993 | Takahashi | |
| 5,259,364 A | 11/1993 | Bob et al. | |
| 5,271,380 A | 12/1993 | Riek et al. | |
| 5,297,536 A | 3/1994 | Wilk | |

(Continued)

FOREIGN PATENT DOCUMENTS

| | | |
|---|---|---|
| EP | 1459688 | 9/2004 |
| EP | 1518499 A1 | 3/2005 |

(Continued)

OTHER PUBLICATIONS

Official Letter from Mexican Institute of Industrial Property, dated Apr. 2, 2009, 3 pages.

(Continued)

*Primary Examiner* — Katherine Dowe

(57) ABSTRACT

Devices are provided herein for translumenal access to a treatment site within a body cavity. In general, the devices include an elongate sleeve configured to provide access to a treatment site wherein various portions of the sleeve are associated with an anti-microbial agent. Additionally, the anti-microbial agent(s) can be disposed within a housing and/or inner lumen of the sleeve such that surgical instruments passing therethrough can be sterilized en route to and/or being withdrawn from the treatment site. Additionally, various methods are also provided herein for maintaining the sterility of a treatment site.

17 Claims, 14 Drawing Sheets

(56) References Cited

U.S. PATENT DOCUMENTS

| | | | |
|---|---|---|---|
| 5,334,150 A | 8/1994 | Kaali | |
| 5,334,166 A * | 8/1994 | Palestrant | 604/265 |
| 5,341,815 A | 8/1994 | Cofone et al. | |
| 5,391,156 A | 2/1995 | Hildwein et al. | |
| 5,429,609 A * | 7/1995 | Yoon | 604/167.03 |
| 5,448,990 A | 9/1995 | De Faria-Correa | |
| 5,458,131 A | 10/1995 | Wilk | |
| 5,518,501 A | 5/1996 | Oneda et al. | |
| 5,569,291 A * | 10/1996 | Privitera et al. | 606/185 |
| 5,569,292 A | 10/1996 | Scwemberger et al. | |
| 5,591,192 A | 1/1997 | Privitera et al. | |
| 5,599,305 A * | 2/1997 | Hermann et al. | 604/95.04 |
| 5,674,184 A | 10/1997 | Hassler, Jr. | |
| 5,685,820 A | 11/1997 | Riek et al. | |
| 5,743,880 A | 4/1998 | Hlavka | |
| 5,756,145 A * | 5/1998 | Darouiche | 427/2.24 |
| 5,817,061 A | 10/1998 | Goodwin et al. | |
| 5,871,440 A | 2/1999 | Okada | |
| 5,897,487 A | 4/1999 | Ouchi | |
| 6,030,365 A | 2/2000 | Laufer | |
| 6,039,725 A * | 3/2000 | Moenning et al. | 606/1 |
| 6,387,043 B1 | 5/2002 | Yoon | |
| 6,432,044 B1 | 8/2002 | Lunsford et al. | |
| 6,440,061 B1 | 8/2002 | Wenner et al. | |
| 6,524,234 B2 | 2/2003 | Ouchi | |
| 6,740,064 B1 * | 5/2004 | Sorrentino et al. | 604/264 |
| 6,869,393 B2 | 3/2005 | Butler | |
| 6,908,428 B2 | 6/2005 | Aizenfeld et al. | |
| 6,918,871 B2 | 7/2005 | Schulze | |
| 7,425,202 B2 | 9/2008 | Huang et al. | |
| 7,485,092 B1 | 2/2009 | Stewart et al. | |
| 7,963,912 B2 | 6/2011 | Zwolinski et al. | |
| 2001/0044595 A1 | 11/2001 | Reydel et al. | |
| 2001/0049497 A1 | 12/2001 | Kalloo et al. | |
| 2002/0004646 A1 | 1/2002 | Manhes | |
| 2002/0077646 A1 | 6/2002 | Truwit et al. | |
| 2002/0133188 A1 | 9/2002 | O'Heeron et al. | |
| 2002/0165521 A1 | 11/2002 | Cioanta et al. | |
| 2003/0105386 A1 | 6/2003 | Voloshin et al. | |
| 2003/0167050 A1* | 9/2003 | Prosl et al. | 604/508 |
| 2003/0225312 A1 | 12/2003 | Suzuki et al. | |
| 2004/0093000 A1 | 5/2004 | Kerr | |
| 2004/0143162 A1 | 7/2004 | Krattiger et al. | |
| 2004/0230165 A1* | 11/2004 | Prosl et al. | 604/265 |
| 2004/0254422 A1 | 12/2004 | Singh | |
| 2004/0254545 A1 | 12/2004 | Rider et al. | |
| 2004/0260245 A1 | 12/2004 | Clem et al. | |
| 2005/0010237 A1 | 1/2005 | Niazi | |
| 2005/0043584 A1 | 2/2005 | Nozue | |
| 2005/0043589 A1 | 2/2005 | Pruitt | |
| 2005/0043682 A1 | 2/2005 | Kucklick et al. | |
| 2005/0059934 A1* | 3/2005 | Wenchell et al. | 604/167.01 |
| 2005/0085773 A1* | 4/2005 | Forsberg | 604/164.01 |
| 2005/0107664 A1 | 5/2005 | Kalloo et al. | |
| 2005/0107816 A1 | 5/2005 | Pingleton et al. | |
| 2005/0203486 A1* | 9/2005 | Sommerich | 604/891.1 |
| 2006/0004254 A1 | 1/2006 | Voloshin et al. | |
| 2006/0015006 A1 | 1/2006 | Laurence et al. | |
| 2006/0079925 A1 | 4/2006 | Kerr | |
| 2006/0111612 A1 | 5/2006 | Matsumoto | |
| 2006/0149305 A1* | 7/2006 | Cuevas et al. | 606/191 |
| 2006/0237022 A1 | 10/2006 | Chen et al. | |
| 2006/0270900 A1 | 11/2006 | Chin et al. | |
| 2007/0123840 A1 | 5/2007 | Cox | |
| 2007/0260117 A1 | 11/2007 | Zwolinski et al. | |
| 2007/0260121 A1 | 11/2007 | Bakos et al. | |
| 2007/0260273 A1 | 11/2007 | Cropper et al. | |

FOREIGN PATENT DOCUMENTS

| | | |
|---|---|---|
| JP | 05-337076 A | 12/1993 |
| JP | 2000300570 A | 10/2000 |
| JP | 2005-525860 A | 9/2005 |
| WO | WO-9915068 | 4/1999 |
| WO | WO-03053261 | 7/2003 |
| WO | 03082122 A1 | 10/2003 |
| WO | 2004/064899 | 8/2004 |
| WO | WO-2005089433 | 9/2005 |

OTHER PUBLICATIONS

European Search Report, Application No. 07251893.9, mailed Jun. 12, 2008, 10 pages.

EP Office Action dated Apr. 29, 2011, App. No. 07251893.9, 7 pages.

Japanese Office Action for Application No. 2007-122627, issued Mar. 13, 2012. (5 pages).

* cited by examiner

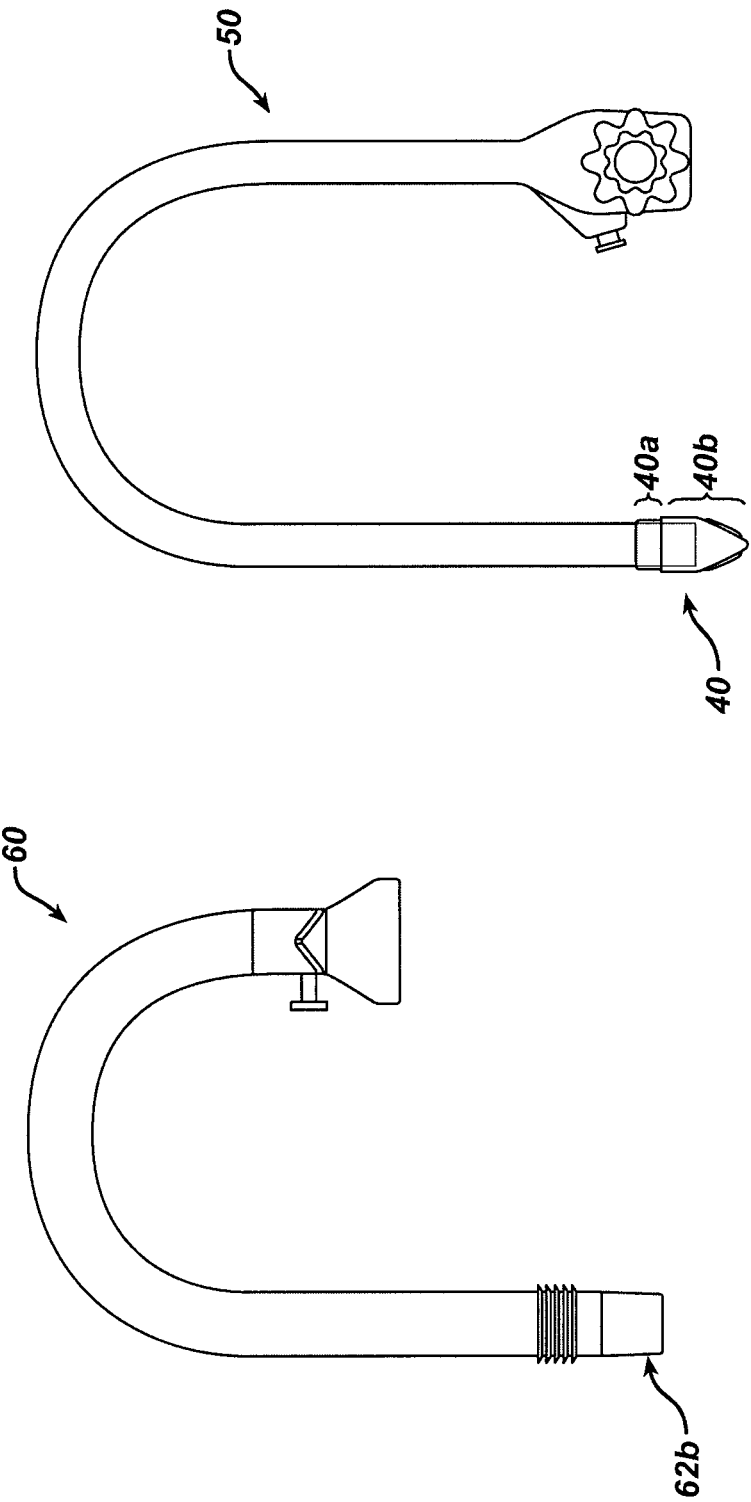

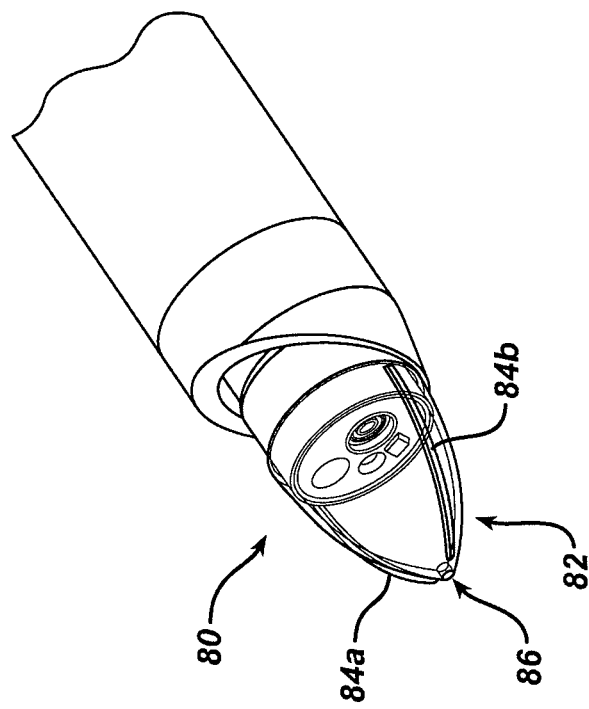
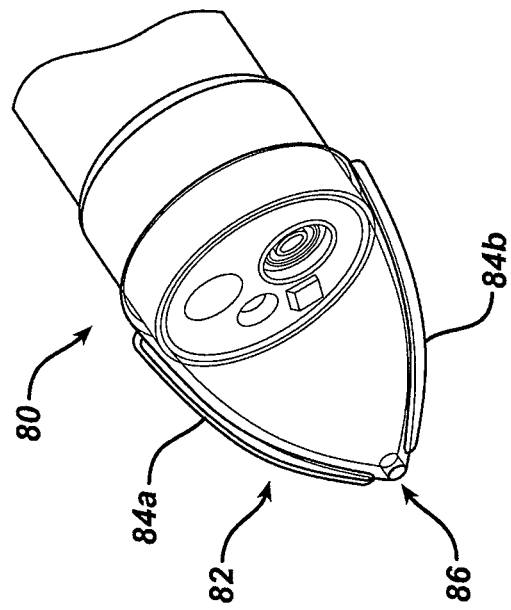

ENDOSCOPIC TRANSLUMENAL SURGICAL SYSTEMS

RELATED APPLICATION(S)

The present application is a continuation-in-part of U.S. patent application Ser. No. 11/382,173, filed on May 8, 2006 and entitled "Endoscopic Translumenal Surgical Systems," the entirety of which is incorporated by reference herein.

FIELD OF THE INVENTION

The present invention relates to methods and devices for endoscopic translumenal surgery.

BACKGROUND OF THE INVENTION

Endoscopic surgery can be used to access the abdominal cavity via natural openings (mouth, anus, vagina, urethra) of the body and through the peritoneal lining of the abdominal cavity. Obviously, the size and shape of instruments that may be passed through a bodily lumen in order to perform a medical procedure in the abdominal cavity are greatly restricted due to the anatomical properties of the lumen. General surgeons, gastroenterologists, and other medical specialists, routinely use flexible endoscopes for intralumenal (within the lumen of the alimentary canal) examination and treatment of the upper gastrointestinal (GI) tract, via the mouth, and the lower GI tract, via the anus. In these procedures, the physician pushes the flexible endoscope into the lumen, periodically pausing to articulate the distal end of the endoscope using external control knobs, to redirect the distal tip of the endoscope. In this way, the physician may navigate the crooked passageway of the upper GI past the pharynx, through the esophagus and gastro esophageal junction, and into the stomach. The physician must take great care not to injure the delicate mucosal lining of the lumen, which generally may stretch open to a diameter in the range of about 15-25 mm, but normally has a non-circular cross sectional configuration when relaxed.

During such translumenal procedures, a puncture must be formed in the stomach wall or in the gastrointestinal tract to access the peritoneal cavity. One device often used to form such a puncture is a needle knife which is inserted through the working channel of the endoscope, and which utilizes energy to penetrate through the tissue. A guidewire is then fed through the endoscope and is passed through the puncture in the stomach wall and into the peritoneal cavity. The needle knife is removed, leaving the guidewire as a placeholder. A balloon catheter is then passed over the guidewire and through the working channel of the endoscope to position the balloon within the opening in the stomach wall. The balloon can then be inflated to increase the size of the opening, thereby enabling the endoscope to push against the rear of the balloon and to be fed through the opening and into the peritoneal cavity. Once the endoscope is positioned within the peritoneal cavity, numerous procedures can be performed through the working channel of the endoscope.

While current methods and devices used to penetrate tissue are effective, one drawback is that several exchanges and steps are required to form the opening in the stomach wall. The small size of the opening formed can also create high resistance to advancing or retracting the endoscope, which is significantly larger than the opening. In the event the endoscope is retracted through the opening, it can also be difficult to locate the opening and re-insert the endoscope. Continued advancement and retraction of the endoscope can also be uncomfortable for the patient. Additionally, such procedures are prone to contamination in light of the repeated insertion and withdrawal of instruments along contaminated environments such as the mouth, esophagus, etc.

Accordingly, there remains a need for improved endoscopic translumenal methods and devices.

SUMMARY

Methods and devices are provided herein for translumenal access to a treatment site within a body cavity. In general, the methods and devices include an anti-microbial agent that is configured to maintain the sterility of a surgical site. For example, the anti-microbial agent can be contained within or coated onto various portions of a medical device, such as a trocar cannula or sleeve and/or an obturator. Additionally, various portions of the elongate sleeve and/or obturator can also be formed from a material which includes an anti-microbial agent. In other embodiments, various seals and/or sponge elements containing an anti-microbial agent (e.g., a coating, a solution, a powder, etc.) can be disposed within a housing and/or disposed within an inner lumen of the sleeve. In an exemplary embodiment, the anti-microbial agent is positioned at one or more locations that are effective to sterilize instruments passing through the device during delivery to and/or withdrawal from a surgical site.

Various embodiments of a translumenal trocar device are provided herein. In one such embodiment, a trocar device is provided which includes a flexible elongate sleeve having an inner lumen extending between proximal and distal ends thereof and forming a working channel for receiving and guiding instruments to a surgical site. The device further includes an anti-microbial agent located within the inner lumen and effective to sterilize instruments passed through the lumen to maintain a sterile surgical site. In one embodiment, the elongate sleeve can include a housing having a seal formed therein and adapted to form a seal around instruments passed through the housing and the elongate sleeve. The anti-microbial agent can be associated with the seal(s). For example, the anti-microbial agent can be in the form of a coating located on the seal, the seal can be formed from a material which includes the anti-microbial agent, and/or the anti-microbial agent can be a solution disposed on the seal.

In another embodiment, the anti-microbial agent can be associated with a sponge element disposed within the an inner lumen of the elongate sleeve, including within a housing portion of the elongate sleeve. Similar to the embodiment discussed above, the anti-microbial agent can be in the form of a coating disposed on a portion of the sponge, and/or an anti-microbial solution disposed on the sponge element. Where the anti-microbial agent is a solution, the device can include a reservoir in fluid communication with the sponge and configured to deliver a desired amount of the anti-microbial solution to the sponge element.

In other embodiments, the anti-microbial agent can be associated with various portions of the elongate sleeve. For example, the anti-microbial agent can be an anti-microbial coating disposed on at least a portion of the elongate sleeve, such as a distal portion of the sleeve, an entire length of the sleeve, inner and/or outer portions of the sleeve, etc. In yet another embodiment, various portions of the elongate sleeve can be formed from a material which includes the anti-microbial agent.

In another embodiment, the device can further include an obturator removably disposable through the lumen in the elongate sleeve, and having a distal end adapted to penetrate through tissue. Similar to above, an anti-microbial agent can be associated with various portions of the obturator. For example, the anti-microbial agent can be a coating disposed on at least a portion of the obturator and/or various portions of the obturator can be formed from a material which includes the anti-microbial agent.

In another embodiment, a translumenal trocar device is provided which includes a flexible trocar sleeve having an elongate tube with a housing formed on a proximal end thereof. The trocar sleeve further includes a lumen extending therethrough, and an obturator disposed through the lumen in the trocar sleeve and having a distal tip that extends distally beyond a distal end of the trocar sleeve such that the distal tip is adapted to guide the obturator and trocar sleeve through tissue. Additionally, the device includes an anti-microbial agent associated with at least one of the trocar sleeve and the obturator.

Various methods for maintaining a sterile surgical site are also provided herein. In one embodiment, the method can include positioning a flexible tube through a body lumen, and inserting an instrument through the flexible tube to position a distal end of the instrument adjacent to a treatment site. The flexible tube can include an anti-microbial agent that sterilizes the instrument as it is passed through the flexible tube. In an exemplary embodiment, the method can include positioning a distal end of the tube adjacent to tissue to be penetrated while a proximal end of the tube remains outside of the patient's body. The method can also include penetrating the distal end of the instrument through the tissue located adjacent to the distal end of the tube to position the distal end of the instrument within a body cavity. The method can further include removing the instrument from the body cavity and from the flexible tube such that the anti-microbial agent associated with the inner lumen of the tube sterilizes the instrument as it is removed. The method can further include introducing a second (or any additional number) of instruments through the flexible tube wherein the anti-microbial agent can sterilize the second instrument as it passed through the flexible tube.

BRIEF DESCRIPTION OF THE DRAWINGS

The invention will be more fully understood from the following detailed description taken in conjunction with the accompanying drawings, in which:

FIG. 5B is a side view of the trocar sleeve of FIG. 5A;

FIG. 5C is a side, partially cross-sectional view of the end cap of FIG. 5A;

FIG. 7B is a perspective view of the tip of FIG. 7A mated to the distal end of an endoscope;

FIG. 7C is a perspective view of the tip and endoscope of FIG. 7B inserted through a trocar sleeve;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1A:
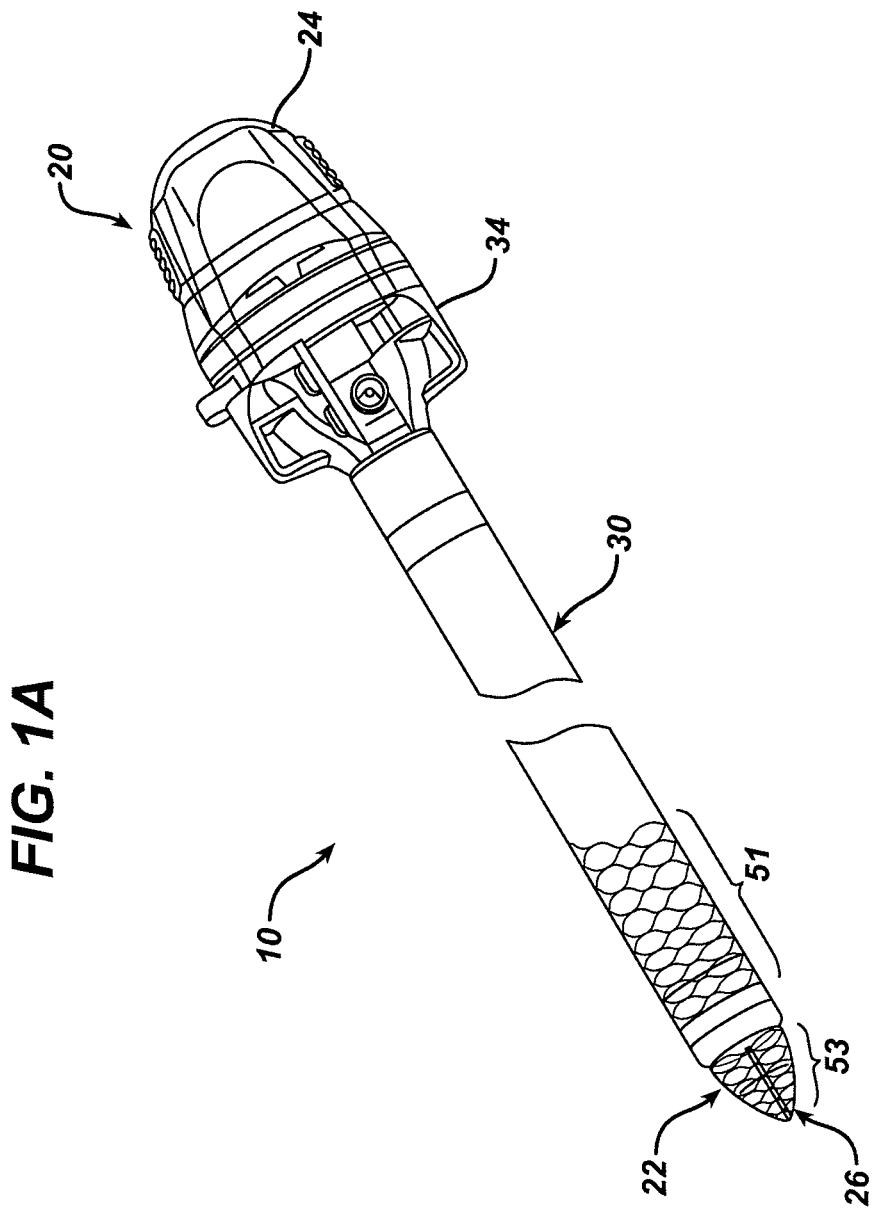
FIG. 1A is a perspective view of one embodiment of a trocar assembly having an obturator that houses an endoscope and a trocar sleeve disposed over the obturator.
Figure 1B:
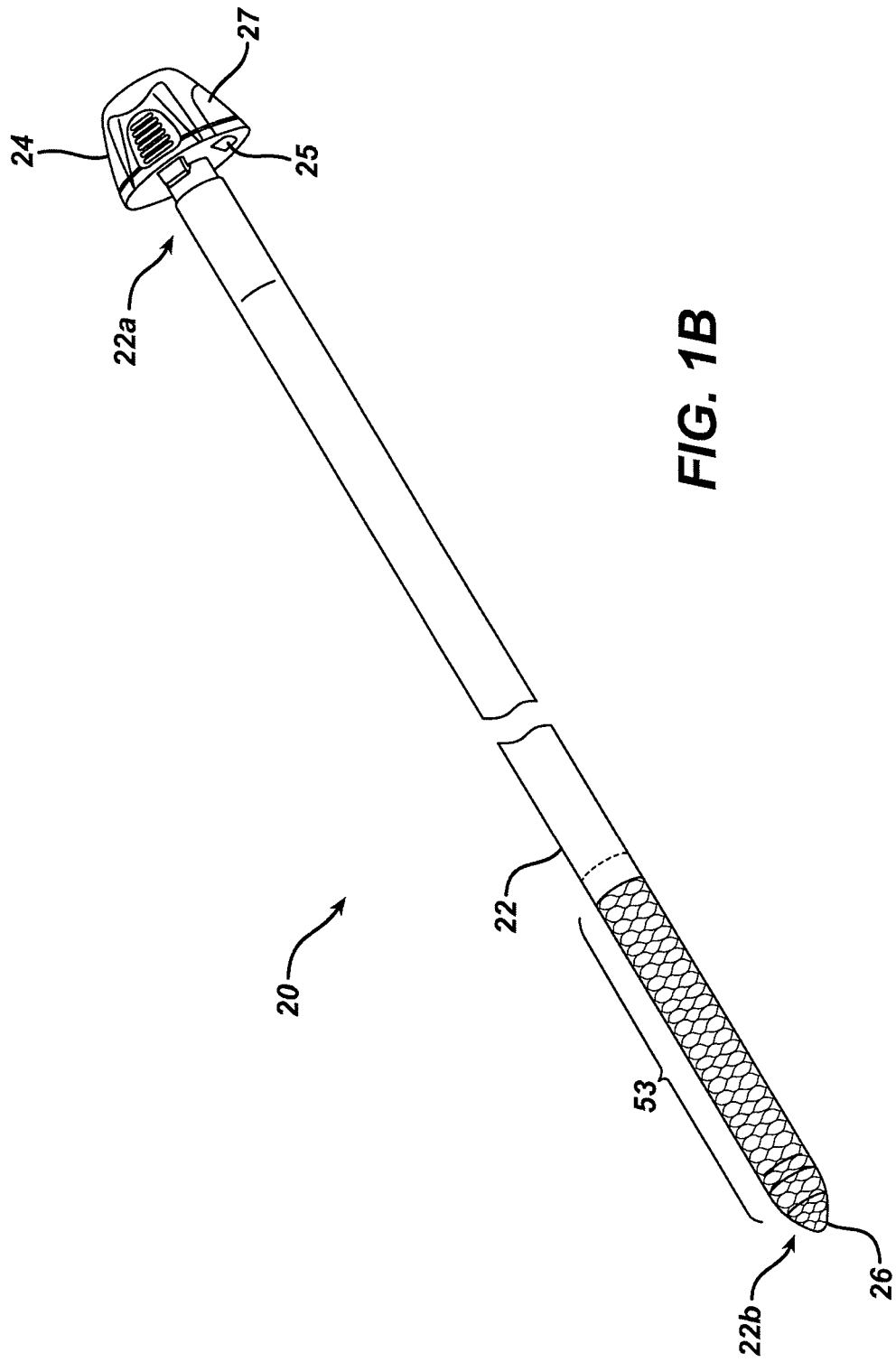
FIG. 1B is a perspective view of the obturator of FIG. 1A.
Figure 1C:
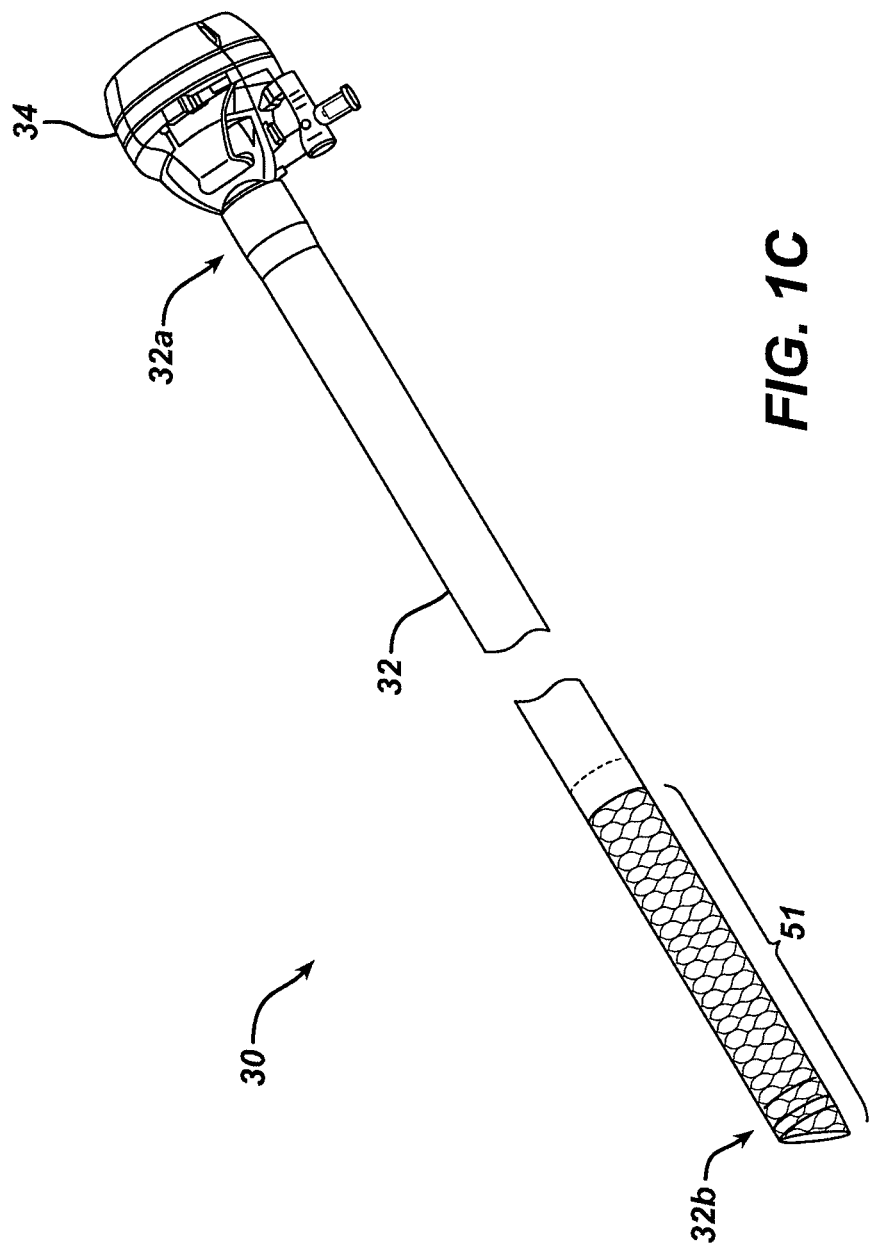
FIG. 1C is a perspective view of the trocar sleeve of FIG. 1A.

The present invention provides devices for maintaining a sterile environment around a treatment site during various translumenal (e.g., transoral and transanal) procedures. In general, the device can be any device having an elongate sleeve with an inner lumen configured for providing surgical access to a treatment site. FIGS. 1A-1C illustrate one exemplary embodiment of such a device 10. As shown, the device 10 includes an obturator 20 slidably disposed within an elongate sleeve 30. Optionally, the elongate sleeve 30 can include a housing 34 disposed at a proximal end of the sleeve 30. In some embodiments, the obturator 20 can also include an inner lumen configured to receive and house an endoscope. To maintain sterility of the treatment site during the procedure, the device 10 can include various anti-microbial agent(s) associated with various portions of the elongate sleeve 30 and/or various portions of the obturator 20. As will be discussed in detail below, the agent can be coated on the elongate sleeve 30 and/or obturator 20, all or portions of the sleeve 30 and/or obturator 20 can be formed of a material which includes the anti-microbial agent, and/or the anti-microbial agent can be a solution that is delivered to the sleeve 30 and/or obturator 20, or to components thereof such as a seal and/or sponge element disposed within the elongate sleeve 30 and/or obturator 20. In use, the anti-microbial agent is effective to sterilize the elongate sleeve 30 and/or instruments (e.g., obturator 20, endoscope, etc.) passing through the sleeve 30.

The obturator 20 is shown in more detail in FIG. 1B, and as shown the obturator 20 includes a hollow, elongate flexible shaft 22 having a proximal end 22a that is coupled to a housing 24 and a distal end 22b with a tip 26 that is adapted to be inserted through tissue. The size of the shaft 22 can vary, but it preferably has a length that allows it to be inserted translumenally, such as through a patient's esophagus. The obturator 20 can optionally have a diameter that allows an endoscope to be received therein. The shaft 22 can be made flexible using various techniques. For example, the shaft 22 can be formed from a flexible material, and/or it can include one or more features formed therein to facilitate flexibility, such as a plurality of cut-outs or slots. For example, certain portions of the shaft 22, such as the distal portion, can be more rigid than other portions of the shaft 22, such as the proximal portion, to correspond to the shape of a body lumen through which the shaft 22 is being inserted. This can be achieved by forming the shaft 22 from different materials, varying the diameter or thickness of the shaft 22, or using various other techniques know in the art. A person skilled in the art will appreciate that the shaft 22 can have virtually any configuration that allows the shaft 22 to flex as it is inserted through a tortuous body lumen. The shaft 22 can also include other features to facilitate use, such as one or more spiral wires embedded therein and configuration to prevent kinking of the shaft 22.

The housing 24 coupled to or formed on the proximal end 22a of the shaft 22 can have a variety of configurations, but in an exemplary embodiment the housing 24 is provided to allow the obturator 20 to removably mate to the elongate sleeve 30. For example, the housing 24 can include one or more mating elements to mate the housing 24 to a housing 34 formed on the elongate sleeve 30, as will be discussed in more detail below. While virtually any mating technique can be used, in the illustrated embodiment the housing 24 on the obturator 20 includes first and second tabs (only one tab 25 is shown) that extend distally from a distal surface of the housing 24. The tabs are configured to extend into corresponding bores formed in the housing 34 on the trocar sleeve 30. The tabs can also include protrusions formed adjacent to a terminal end thereof to allow the tabs to be engaged by an engagement mechanism formed within the bores, thereby fixedly mating the housing 24 on the obturator 20 to the housing 34 on the elongate sleeve 30. A release mechanism can be used to release the obturator 20 from the trocar sleeve 30. As shown in FIG. 1B, the first and second tabs are coupled to deflectable members (only one tab 25 and one deflectable member 27 is shown) that extend from opposed lateral sides of the housing 24. The deflectable members can be depressed to cause the tabs to move, thereby releasing the tabs from the engaging mechanism formed in the bores in the trocar sleeve 30. The housing 24 can also optionally include a lumen (not shown) formed therethrough for receiving an endoscope to allow the endoscope to be advanced into the obturator 20. A person skilled in the other will appreciate that various other techniques can be used to mate the housing 24 of the obturator 20 to the housing 34 of the elongate sleeve 30, including twist-lock mechanisms, threads, snap-fit, interference fit, etc. While not shown, where the obturator 20 is configured to receive an endoscope, an opening formed in the proximal-most end of the housing 24 can optionally include a seal disposed therein and effective to engage an outer surface of the endoscope to seal the endoscope with respect to the obturator 20. The seal is particularly useful during insufflation as it can prevent gases from escaping through the assembly. In particular, the seal can permit the passage of the obturator 20 and endoscope through the trocar sleeve 30 while limiting or preventing the passage of fluid or gas therethrough. A person skilled in the art will appreciate that the housing can include various other features known in the art, and that the housing can have virtually any shape and size. The obturator 20 also does not need to include a housing, but rather can merely be an elongate shaft that is slidably disposable through a trocar sleeve.

The tip 26 on the distal end 22b of the elongate shaft 22 of the obturator 20 can also have a variety of configurations. For example, the tip 26 can be tapered, include blades or wings for cutting and/or separating tissue. A person skilled in the art will appreciate that various configurations of the tip are within the spirit and scope of the present invention. Where the obturator 20 is configured to receive an endoscope, the distal end 22b can be transparent to facilitate viewing therethrough.

The device 10 also includes an elongate sleeve 30, which is shown in more detail in FIG. 1C. While the elongate sleeve 30 can have virtually any configuration, it preferably includes a hollow, elongate flexible shaft 32 that is configured to provide surgical access to a treatment site. In those embodiments utilizing an obturator 20, the outer sleeve 30 can configured to be slidably disposed over the obturator 20. The size of the flexible shaft 32 of the outer sleeve 30 can vary, but it preferably has a length that is slightly less then a length of the shaft 22 of the obturator 20 such that the tip 26 of the obturator 20 extends distally beyond a distal end 32b of the elongate shaft 32. The diameter can also vary, but as indicated above, the diameter should be sufficient to allow the elongate shaft 32 of the trocar sleeve 30 to receive the elongate shaft 22 of the obturator 20 therein. The elongate shaft 32 of the trocar sleeve 30 can be made flexible using various techniques known in the art, including those previously discussed with respect to the elongate shaft 22 of the obturator 20. In an exemplary embodiment, the trocar sleeve 30 is a flexible sleeve having a coiled wire wrapped there around or embedded therein to prevent kinking, and having an interior lining configured to facilitate smooth passage of the obturator 20 therethrough. The elongate shaft 32 of the trocar sleeve 30 can also include regions that vary in flexibility, as was also discussed above with respect to the elongate shaft 22 of the obturator 20. The trocar sleeve 30 can also include other features to facilitate use of the trocar sleeve 30 with the obturator 20. For example, the distal end 32b of the trocar sleeve 30 can have an outer diameter that tapers distally, as shown, to form a substantially smooth continuous transition from the trocar sleeve 30 to the tip 26 of the obturator 20. The distal end 32b can also be angled as shown, or it can have various other configurations.

Figure 2:
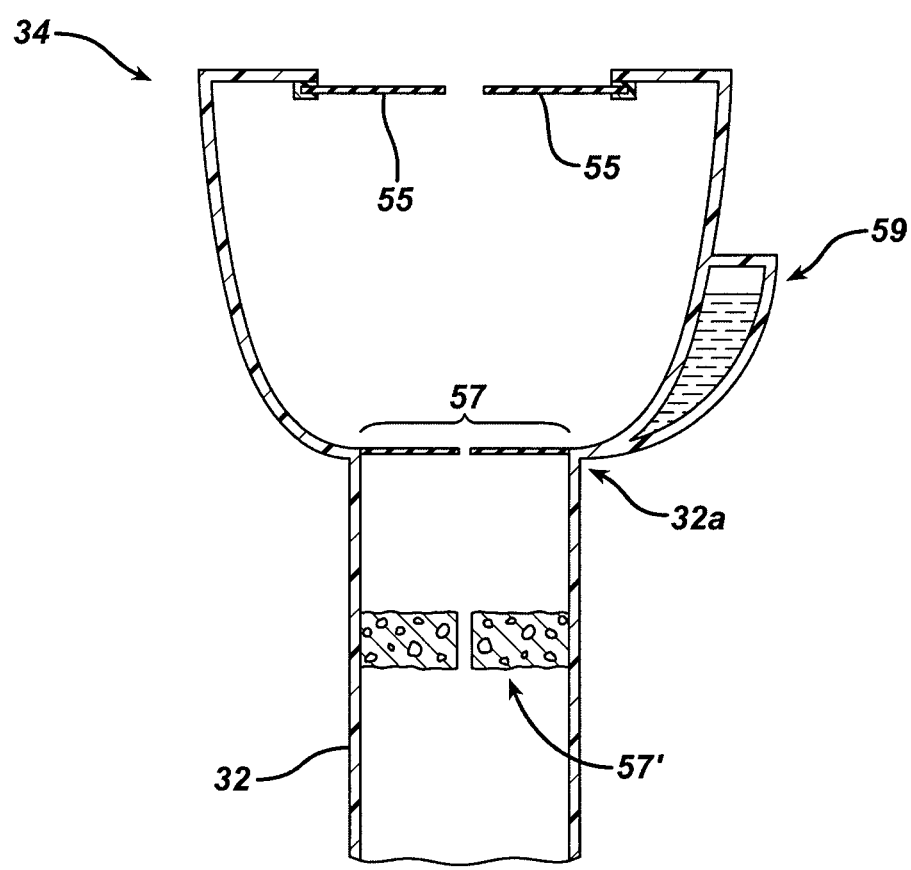
FIG. 2 is a cross-sectional view of a housing portion of the trocar sleeve of FIG. 1C.

The trocar sleeve 30 can also including a housing 34 formed on or coupled to a proximal end 32a of the elongate shaft 32. The housing 34 can be configured to removably mate to the housing 24 of the obturator 20, and in particular the housing 34 can include a proximal end with first and second bores (not shown) formed thereon and configured to receive the tabs formed on the distal end of the housing 24 on the obturator 20, as previously explained. As shown in FIG. 2, the housing 34 can also include an inner lumen formed therethrough and coaxial with the lumen in the elongate shaft 32 to allow the elongate shaft 22 of the obturator 20 to be inserted through the housing 34 and into the elongate shaft 32 of the trocar sleeve 30. Also, one or more seals 55, 57 can be disposed within the lumen in the housing 34 to engage an outer surface of the shaft 22 of the obturator 20 or other devices inserted therethrough to seal the shaft 22 of the obturator 20 or the device with respect to the trocar sleeve housing 34. Various seals or valve mechanisms are known in the art, including duck bill or double duck bill valves, zero-closure valves, septums, gaskets, etc. A person skilled in the art will appreciate that the housing 34 can include various other features known in the art, and that the housing 34 can have virtually any shape and size. Alternatively, the elongate sleeve 30 does not need to include any housing and can merely be in the form of an elongate shaft.

In an exemplary embodiment, the device 10 further includes an anti-microbial agent associated with various portions of the elongate sleeve 30 and/or the obturator 20. As previously indicated, the anti-microbial agent can be formed on, formed integrally with, and/or delivered to portions of the sleeve 30 and/or obturator 20 to sterilize instruments passing therethrough. FIG. 1C shows one exemplary embodiment of an anti-microbial agent located on a distal portion 51 of the elongate sleeve 30. For example, the anti-microbial agent can include a coating that is applied to the distal portion 51 of the elongate sleeve 30, preferably within the inner lumen of the sleeve 30 such that it contacts instruments inserted through the sleeve 30. As will be apparent to those skilled in the art, the anti-microbial coating can be formed from any anti-microbial material or combination of such materials capable of providing the desired anti-microbial effect. For example, in an exemplary embodiment, the coating can include ionic silver, which is an excellent antimicrobial, with relatively low toxicity against non-target organisms. In other embodiments, the distal portion 51 of the elongate sleeve 30 can be formed from a material that includes the anti-microbial agent. Like above, such a material and/or anti-microbial agent can include any such material and/or agent capable of providing the desired effect. Those skilled in the art will appreciate that the anti-microbial agent can be associated with virtually any portion of the sleeve 30, including along the entire sleeve 30, along any length of the sleeve 30, or along multiple portions of the sleeve 30.

Similarly, as shown in FIG. 1B, in those embodiments utilizing an obturator 20, an anti-microbial agent can also or alternatively be associated with a portion of the obturator 20, such as a distal portion 53 thereof. In an exemplary embodiment, the anti-microbial agent is located along a length of the obturator 20 that is passed through tissue and into a body cavity (e.g., the abdominal cavity). In other embodiments, where the obturator 20 includes an inner lumen, the anti-microbial agent can be located within the inner lumen of the obturator 20 (such as in those embodiments wherein the obturator 20 includes an inner lumen configured to receive and/or house an endoscope). Like above, the anti-microbial agent can be associated with any portion of the obturator 20, and it can be in the form of a coating or solution delivered to the obturator, or portions of the obturator 20 can be formed from a material (or various materials) which includes the anti-microbial agent.

In another embodiment, the anti-microbial agent can be associated with a seal 57 disposed within the housing and/or a sponge element 57' disposed within the inner lumen of the elongate sleeve 30 and/or obturator 20. For example, as shown in FIG. 2, an anti-microbial agent can be associated with at least one of the seals 55,57 disposed within the housing 34 of the sleeve 30 such that the anti-microbial agent contacts and thereby sterilizes any instrument passing through the seal 55, 57. Like above, the anti-microbial agent can be a coating formed on the seal 55, 57 and/or the seal 55, 57 can be at least partially formed of a material which includes the anti-microbial agent. For example, the anti-microbial agent can be a powder disposed on the seal 55, 57. In another embodiment, the anti-microbial agent can be an anti-microbial solution that is delivered to the seal 55, 57 thereby allowing the solution to be transferred from the seal 55, 57 to any surgical instrument passing therethrough. The seal 55, 57 can also or alternatively be configured to provide an antiseptic solution to any instrument passing therethough. For example, the solution can include a povidone-iodine solution (e.g., polyvinyl pyrrilidine triiodine solution). Additionally, the solution can include various surfactants so as to reduce the surface tension of water and enable any surface active agents to work efficiently. In other embodiments, the solution can further include various anti-biotic solutions. Those skilled in the art will appreciate that any such solution capable of producing any desired therapeutic effect is within the spirit and scope of the present invention.

Figure 3:
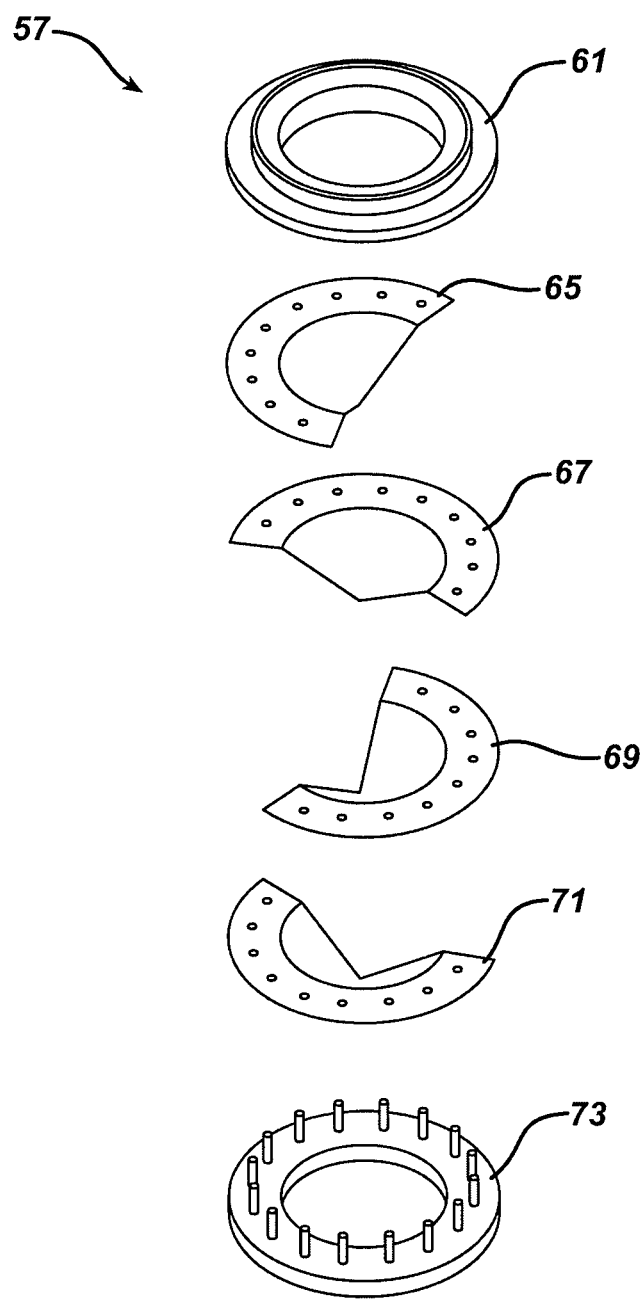
FIG. 3 is an exploded view of one embodiment of a seal capable of being disposed within the housing of FIG. 2.

FIG. 3 provides an exploded view of an embodiment of a seal 57, however a person skilled in the art will appreciate that any seal can be used. As shown, the seal 57 includes a top frame 61, a bottom frame 73, and a number of over-lapping layers 65, 67, 69, 71 disposed therebetween. In use, the various over-lapping layers 65, 67, 69, 71 can be configured to retain an amount of the anti-microbial solution and/or powder therebetween. As a surgical instrument is passed therethrough, the solution can be transferred from the seal 57 to the instrument thereby sterilizing the instrument. In another embodiment, the seal can be a thin single opening lip seal. For example, such a lip seal would have a thickness of about 0.005 inches to about 0.010 inches. As will be appreciated by those skilled in the art, the seal can have any configuration effective to transfer an anti-microbial agent to a surgical instrument passing therethrough.

In other embodiments, as shown in FIG. 2, the device 10 can include at least one sponge element 57' disposed within the inner lumen of the elongate sleeve 30. Similar to the seal 57, an anti-microbial agent (preferably, a solution) can be associated with the sponge 57' such that the agent can be transferred from the sponge 57' to any surgical instrument passing therethrough. As will be apparent to those skilled in the art, the sponge element 57' can be formed from any material and can have any configuration capable of retaining an amount of the anti-microbial agent and transferring an amount of the agent to the instrument passing therethrough. Moreover, the sponge element 57' can be located within various portions of the lumen, including within the housing 34 at the distal end of the shaft 32.

Figure 4A:
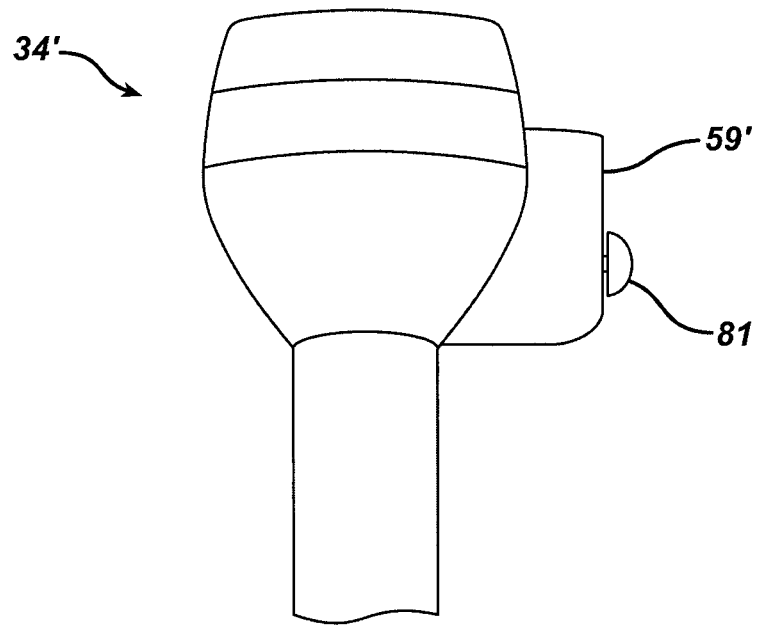
FIG. 4A is a perspective view of another embodiment of a housing portion of a trocar sleeve having a reservoir for delivering an anti-microbial agent to a lumen of the trocar sleeve.
Figure 4B:
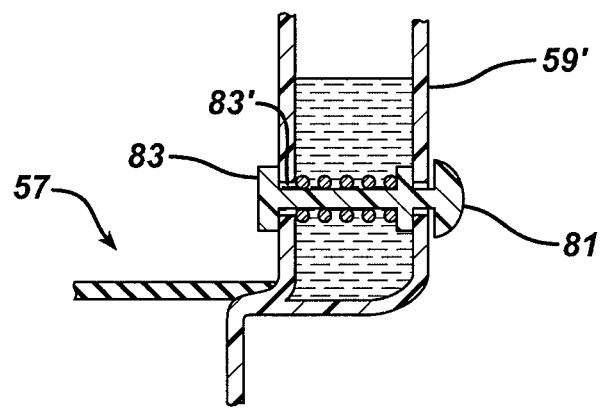
FIG. 4B is a cross sectional view of a portion of the housing of FIG. 4A.

In various embodiments, the seal 57 and/or sponge element 57', or the lumen itself, can be in fluid communication with a reservoir 59 such that the reservoir 59 is capable of delivering an amount of an anti-microbial solution from the reservoir 59 to the seal 57, sponge element 57', or other regions of the device. The reservoir 59 can have various configurations capable of controllably delivering the anti-microbial agent from the reservoir 59 to the seal 57, sponge element 57', or lumen. For example, the reservoir 59 can include a valve element capable of controlling flow from the reservoir to the seal 57, sponge 57', or lumen. In an exemplary embodiment shown in FIGS. 4A-4B, the reservoir 59 can include a push-button valve. As shown, the valve includes an exterior button 81 which can be biased by any number of well-known mechanisms in an extended position. As the button 81 is depressed by a user, a distal stopper 83 can be pushed inward and away from an opening 83' thereby allowing the anti-microbial agent to dispense from the reservoir 59 through the opening 83' to the seal 57, sponge elements 57', or other regions of the device.

In use, referring back to FIG. 1A, the obturator 20 can be inserted through and mated to the elongate sleeve 30 (e.g., a trocar sleeve) to form a flexible trocar assembly 10 that can be used to form a pathway into a body lumen. In particular, the obturator 20 can be inserted through the opening in the housing 34 of the trocar sleeve 30, and the housing 24 on the obturator 20 can be mated to the housing 34 on the trocar sleeve 30. As a result, the tip 26 of the obturator 20 will extend distally beyond the distal end 32b of the trocar sleeve 30. At least the distal end of the assembly 10 can be inserted translumenally, e.g., transorally or transanally, through a body lumen, and it can be inserted through tissue to gain access to a body cavity. Exemplary methods for inserting the assembly translumenally and through tissue will be discussed in more detail below.

Figure 5A:
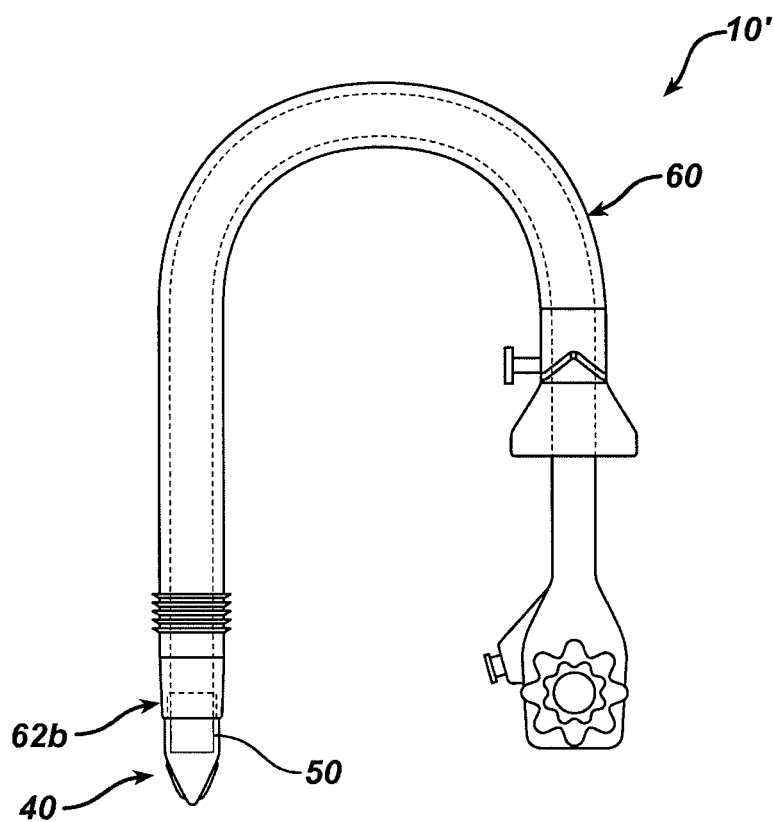
FIG. 5A is a side, partially cross-sectional view of another embodiment of a trocar assembly having an end cap mated to a distal end of an endoscope that is inserted through a trocar sleeve.

In another embodiment, rather than using an obturator 20 for inserting the trocar assembly 10 through tissue, an end cap, having a configuration similar to the tip 26 at the distal end 22b of the obturator 20, can be removably mated to the distal end of the endoscope. This is illustrated in FIGS. 5A and 5C, which show an end cap 40 removably mated to a distal end of an endoscope 50. The end cap 40 and endoscope 50 can optionally be inserted through a trocar sleeve 60, as shown in FIGS. 5A and 5B, to form a trocar assembly 10' that is similar to the trocar assembly 10 previously described with respect to FIGS. 1A-1C. While not described in detail, the trocar sleeve 60, shown separately in FIG. 5B, can have a configuration that is similar to the trocar sleeve 30 previously described with respect to the embodiment shown in FIGS. 1A-1C. In use, the end cap 40 can be mated to the distal end of the endoscope 50, and the endoscope 50 and end cap 40 can optionally be inserted through the trocar sleeve 60 to form a trocar assembly 10'. As previously explained with respect to the trocar sleeve 30 of FIG. 1C, the trocar sleeve 60 of FIG. 5A can include one or more seals disposed therein and effective to form a seal with the endoscope 50 inserted therethrough. As further shown in FIG. 5A, when the endoscope 50 is inserted through the trocar sleeve 60, the end cap 40, or at least the tip portion 40b of the end cap 40, will extend distally beyond a distal-most end 62b of the trocar sleeve 60 to allow the tip portion 40b of the end cap 40 to facilitate insertion of the assembly through tissue. The distal end 62b of the sleeve 60 can have various configurations, as previously explained, to allow the sleeve 60 and end cap 40 to fit together and have a substantially smooth continuous outer surface. Once the assembly is fully mated, at least the distal portion of the assembly can be inserted translumenally, e.g., transorally or transanally, through a body lumen, and it can be inserted through tissue to gain access to a body cavity. Exemplary methods for inserting the assembly translumenally and through tissue will be discussed in more detail below.

The end cap 40 can have a variety of configurations, and various techniques can be used to mate the end cap 40 to the distal end of an endoscope 50. In one exemplary embodiment, shown in detail in FIG. 5C, the end cap 40 can have a substantially cylindrical proximal portion 40a that can be slidably disposed over a substantially cylindrical distal end of the endoscope 50. The shape can, however, vary depending on the shape of the endoscope 50. The proximal portion 40a of the end cap 40 can also be configured to releasably engage the endoscope 50 to prevent the end cap 40 from disengaging with the endoscope 50 during use of the device. This can be achieved using, for example, a resilient material, an interference fit, a snap-fit, threads, or various other mating techniques known in the art. As further shown in FIG. 5C, the end cap 40 can also include a distal tip portion 40b that can be configured to facilitate insertion of the endoscope 50 through tissue. The particular configuration of the distal tip 40b can vary, and various exemplary distal tips will be discussed in more detail below with respect to FIGS. 6A-8.

Figure 6A:
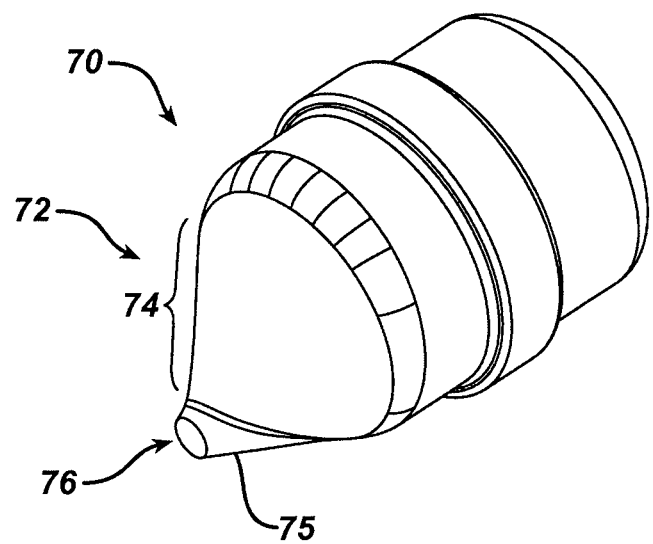
FIG. 6A is a perspective view of one exemplary embodiment of a tip configuration for use with the obturator of FIG. 1A or the end cap of FIG. 5A.
Figure 6B:
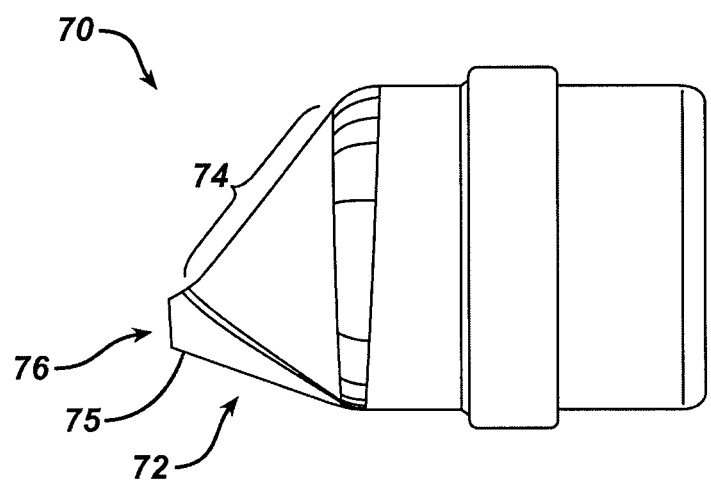
FIG. 6B is a side view of the tip of FIG. 6A.
Figure 7A:
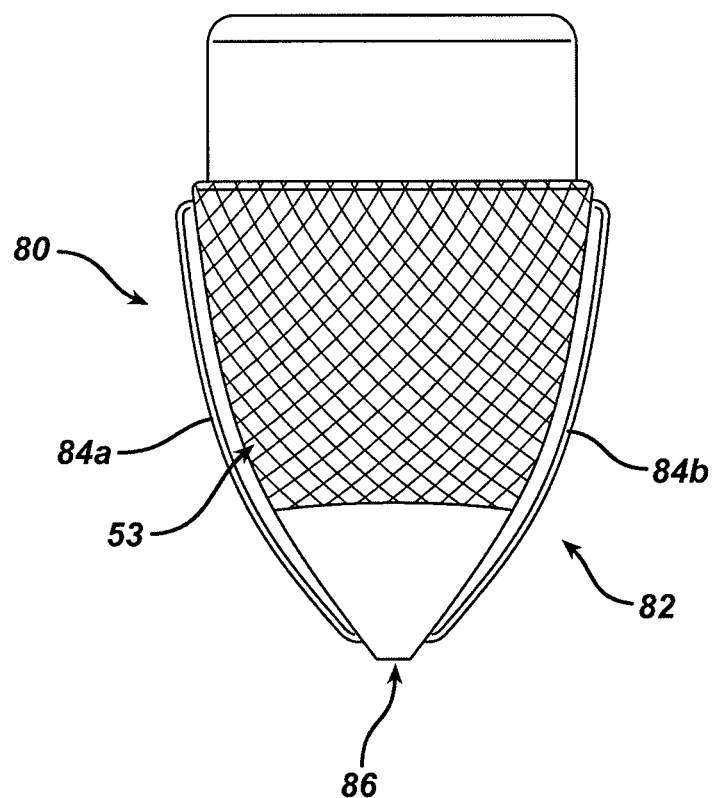
FIG. 7A is a side view of another exemplary embodiment of a tip configuration for use with the obturator of FIG. 1A or the end cap of FIG. 5A.

The tip 40b at the distal end of the end cap 40 can have a variety of configurations depending on the intended use. In an exemplary embodiment, at least a portion and more preferably all of the tip is transparent or clear to allow an image gathering unit at the distal end of the endoscope to view and gather images through the tip. This will allow the endoscope to be used to guide the assembly through a body lumen and through tissue. The particular configuration of the transparent portion can vary in order to further facilitate viewing through the tip. For example, the materials and shape can be optimized to provide a smooth, clear viewing surface through which the endoscope can view and gather images. In one exemplary embodiment, the tip can be shaped so that a region of the tip is relatively flat. This is illustrated in the embodiment shown in FIGS. 6A-6B, which illustrate an end cap 70 having a tip 72 with a distal-most region 74 that has a minimal curvature such that the region 74 is somewhat flattened. In another exemplary embodiment, as shown in FIGS. 7A-7C, the tip 82 can taper distally and it can be in the shape of a parabola to prevent distortion of images gathered therethrough. The tip can also or alternatively be configured to enlarge an opening in tissue as the tip is advanced through the tissue. As is shown in FIG. 7A, similar to the various embodiments discussed above, a portion 53 of the tip 82 can also include an anti-microbial agent. A person skilled in the art will appreciate that the tip can have a variety of configurations to facilitate viewing therethrough.

The particular configuration of the tip can also vary depending on the intended use of the tip. In one embodiment, the tip can have a configuration that allows the tip to cut and penetrate tissue through tissue. This can be achieved, for example, using one or more blades or cutting surfaces formed on the tip. FIGS. 7A and 7B illustrate one embodiment of an end cap 80 having a tip 82 with first and second cutting blades 84a, 84b formed on opposed sides thereof and extending between proximal and distal ends of the tip 82. The cutting blades 84a, 84b protrude above the outer surface of the tip 82, and have sharp edges to cut through tissue. The cutting blades 84a, 84b can also be configured to couple to an energy source to facilitate cutting of tissue. For example, a cautery wire can be coupled to the blades and it can extend through the endoscope attached to the end cap 80 to allow a proximal end of the wire to connect to an energy source. In another embodiment, the blades can be in the form of paddles that do not cut tissue, but rather merely extend outward from an outer surface of the tip. The paddles can have a generally planer, elongate configuration, and in use they can be configured to separate a cut or slit formed in tissue. For example, the paddles can be rotated to spread open an elongate cut made through tissue. The cutting blades can also be used to spread apart tissue, and/or to facilitate enlargement of a puncture hole formed through tissue. A person skilled in the art will appreciate that the cutting blades can be formed integrally with the tip, such that the tip and blades are formed as a single piece of material, or they can be separate from and mated to the tip. As previously mentioned, the tip can also taper distally to facilitate insertion and penetration through tissue. As further shown in FIGS. 7A-7C, the tip 82 can also include other features such as a bore 86 formed in the distal-most end thereof and configured to receive an endoscopic accessory therethrough, such as a guide wire, or a cutting element such as a needle knife or sphinctertome. The assembly can be inserted translumenally along the endoscopic accessory, or the endoscopic accessory can be introduced into the device at various stages of a procedure.

In another embodiment, rather than being configured to penetrate through tissue, the tip can be configured to facilitate insertion through the tissue and a separate endoscopic accessory can be used in coordination with the tip. For example, as previously described, FIGS. 6A-6B illustrate a tip 72 having a region 74 that is substantially planar. As further shown, the tip 72 can also include a protruding portion with a bore 76 formed therein for receiving an endoscopic accessory, such as a guide wire or a cutting tool, such as a needle knife or sphinctertome. The protruding portion 75 can be centrally located, but in an exemplary embodiment it is offset from a central axis of the endoscope so as to allow the protruding portion 75 to be positioned in axial alignment with a working channel of the endoscope, and to the allow the planar region 74 to be positioned in axial alignment with the viewing element in the endoscope. The protruding portion 75 can also taper distally toward the bore 76 to facilitate insertion of the tip through tissue.

Figure 8:
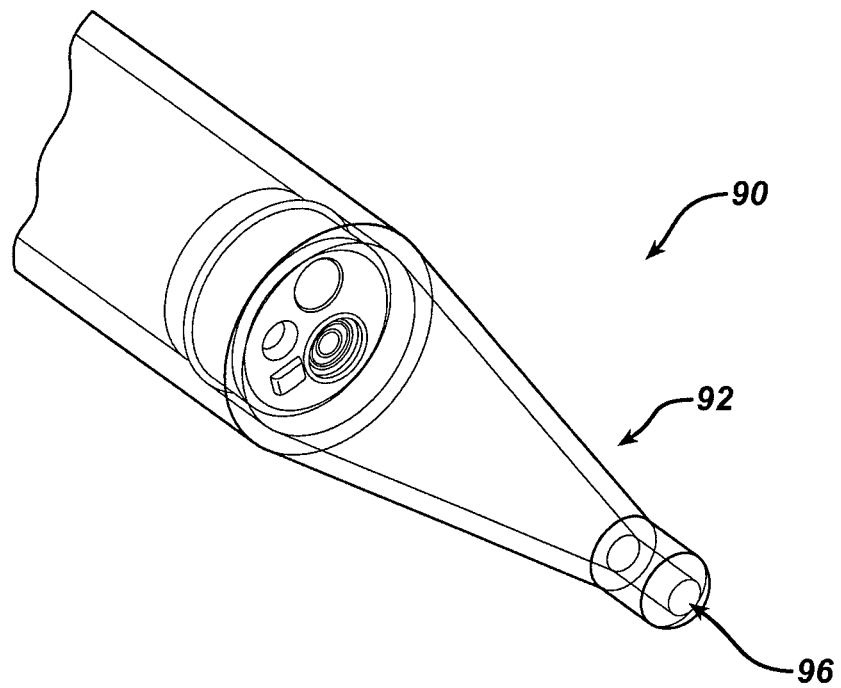
FIG. 8 is a perspective view of another embodiment of a tip configuration for use with the obturator of FIG. 1A or the end cap of FIG. 5A, showing the tip formed on the distal end of an obturator.

FIG. 8 illustrates another embodiment of a tip 92, shown formed on the distal end of an obturator 90, that is preferably configured to be used in combination with an endoscopic accessory, such as a guide wire or a cutting tool, such as a needle knife or sphinctertome. In this embodiment, the tip 92 has a generally conical configuration and tapers distally toward an opening or bore 96 formed in the distal-most end thereof. The bore 96 is co-axial with an axis of the endoscope, however since the tip 92 has an elongated length, any endoscopic accessory inserted through a working channel of the endoscope can move inward to be inserted through the bore 96.

A person skilled in the art will appreciate that the tip of the obturator or the end cap can have a variety of other configurations, and the tips shown in the figures are merely exemplary embodiments of tip configurations. By way of non-limiting example, various other exemplary tip configurations are disclosed in U.S. Pat. No. 5,591,192 of Privitera et al. entitled "Surgical Penetration Instrument Including an Imagining Element", and U.S. Pat. No. 5,569,292 of Scwemberger et al. entitled "Surgical Penetration Instrument With Transparent Blades and Tip Cover," which are hereby incorporated by reference in their entireties. The tip can also include other features. By way of non-limiting example, the tip can be configured to be energized to facilitate insertion and/or penetration of the tip through tissue.

Figure 9A:
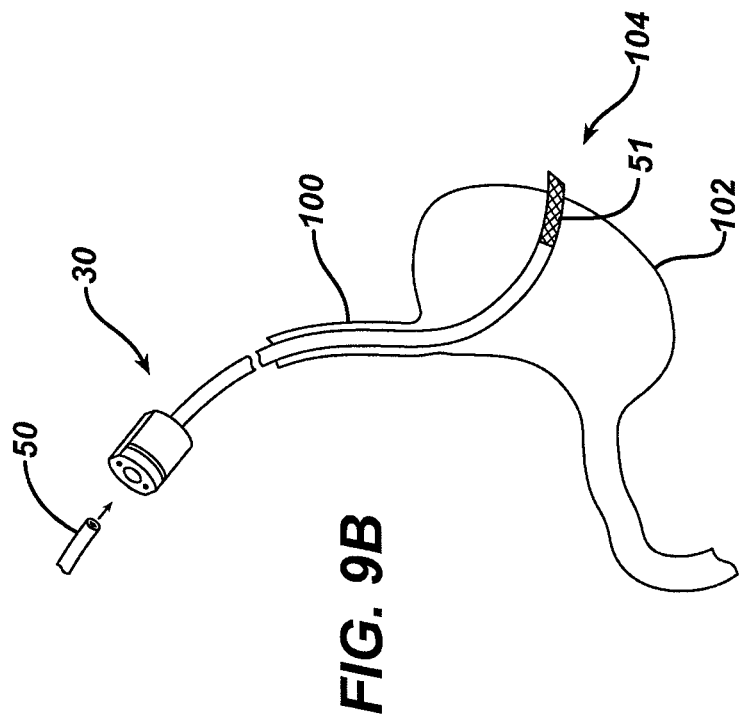
FIG. 9A is an illustration showing the trocar assembly of FIG. 1A inserted translumenally through an esophagus with the distal end penetrated through the stomach wall.
Figure 9B:
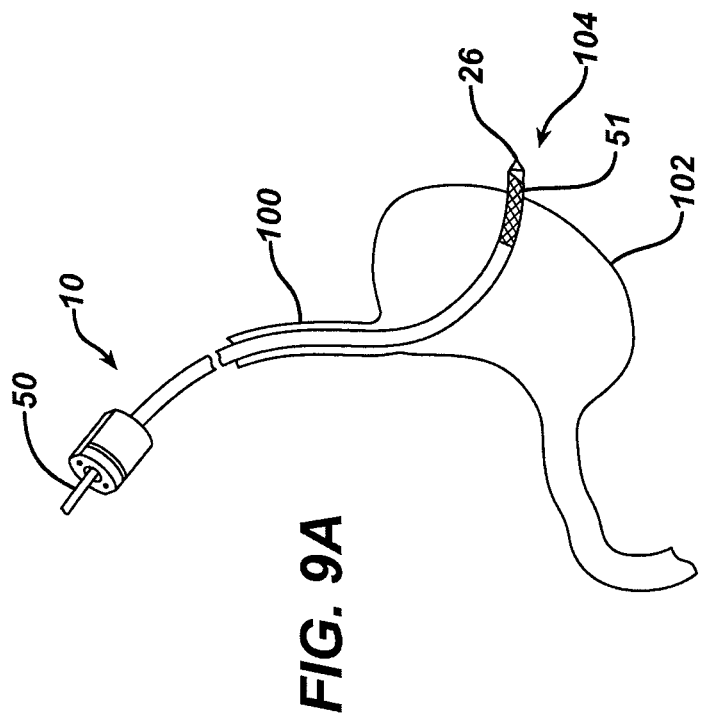
FIG. 9B is an illustration showing the trocar assembly of FIG. 9A, with the obturator and endoscope removed from the trocar sleeve, and the endoscope about to be re-inserted through the trocar sleeve.

Various embodiments of a method for providing a sterile surgical site are also provided herein. As discussed in detail above, the device 10 can include an anti-microbial agent associated with the elongate sleeve 30 and/or the obturator 20, such as an anti-microbial seal 57 and/or sponge element 57' can be disposed within the housing 34 and/or inner lumen of the elongate sleeve 30 of the device, or a coating or material containing an anti-microbial agent and located within the inner lumen of the sleeve 30 or located on or within the obturator 20. In light of these various anti-microbial agents, various translumenal procedures can be performed while minimizing any contamination of the treatment site which can occur as bacteria is carried from the body lumen into the body cavity. As shown in FIGS. 9A-9B, the method can include positioning a flexible tube through a body lumen (e.g., the esophagus) 100. Next, the method can include inserting an instrument through the flexible tube to position a distal end of the instrument adjacent to a treatment site wherein the flexible tube includes an anti-microbial agent that sterilizes the instrument as it is passed through the flexible tube. In an exemplary embodiment, positioning the flexible tube can include positioning a distal end of the tube adjacent a tissue to be penetrated, and a proximal end of the tube remaining outside of a patient's body. Further, the method can also include penetrating the distal end of the instrument (e.g., the obturator or any other instrument) through the tissue located adjacent to the distal end of the tube to position the distal end of the instrument within the body cavity (e.g., the abdominal cavity).

In an alternative embodiment, the method can include removing the instrument from the body cavity and the flexible tube wherein the inner lumen of the flexible tube can be configured to sterilize the instrument as the instrument is withdrawn from the treatment site (e.g., by withdrawing the instrument through the seal and/or sponge element). The method can further include introducing a second instrument through the flexible tube wherein the anti-microbial agent associated with the inner lumen of the tube can also sterilize the second instrument. Additionally, the method can include inserting and withdrawing any number of instruments through the inner lumen wherein the inner lumen is configured to sterilize the various instruments passing therethrough.

FIGS. 9A and 9B also illustrate an embodiment of a method for introducing an endoscope translumenally. The method is shown in conjunction with the device of FIGS. 1A-1C, however a person having ordinary skill in the art will appreciate that the device of FIGS. 5A-5C can be used, and that the device can have various other configurations, as previously described herein and as known in the art. In general, assembled device 10 is inserted translumenally, e.g., transorally or transanally, to position the distal end of the assembly at a desired location at which tissue is to be penetrated. As shown, the assembly is inserted transorally through a patient's esophagus 100 to position the distal end of the device within the stomach 102, and to subsequently penetrate through the stomach wall to position the distal end within the abdominal cavity 104. The device 10 can optionally be guided through the body lumen using a steering mechanism on the endoscope 50, using a steering mechanism that is coupled to the trocar assembly, or using other techniques known in the art.

Once the distal end of the trocar assembly 10, and optionally an endoscope 50 disposed therethrough, are positioned at the desired tissue penetration site, e.g., in the stomach 102, the tip 26 can be inserted through tissue. As previously explained, various techniques can be used to penetrate through the tissue. In the embodiment shown in FIGS. 1A-1C and FIGS. 9A-9B, the tip 26 of the obturator 20 includes cutting blades formed thereon that can cut through tissue, allowing the trocar assembly 10 to be directly penetrated through the tissue. The cutting blades can optionally be connected to an energy source to cauterize the tissue as the tip 26 is inserted therethrough. Where the tip 26 does not include cutting blades, such as the tip 72 shown in FIGS. 6A-6B, or in addition to the cutting blades, a cutting tool, such as a needle knife or sphinctertome, can be inserted through the working channel of the obturator, or the endoscope 50 if used, and through the bore 76 in the tip 72. The needle knife or sphinctertome can then be energized to penetrate or cut through the tissue. The assembly can be guided over the needle knife or sphinctertome to guide the tip 72 through the puncture formed in the tissue by the needle knife, or alternatively the cutting device can be replaced by a guide wire and the assembly can be guided over the guide wire through the puncture. A person skilled in the art will appreciate that various other techniques can be used to penetrate through the tissue.

Once the distal end of the assembly 10 is inserted through the tissue, as shown in FIG. 9A, the obturator 20 and endoscope 50 if used (or, for the embodiment of FIGS. 5A-5C, the end cap 40 and endoscope 50) can be removed from the trocar sleeve 30. The trocar sleeve 30 will function as a placeholder for the puncture formed in the tissue, as the trocar sleeve 30 will remain extending through the puncture and into the body cavity, e.g., the abdominal cavity, as shown in FIG. 9B. Where an endoscope is used, the endoscope 50 can then be removed from the obturator 20 (or, for the embodiment of FIGS. 5A-5C, the end cap 40 can be removed from the endoscope 50), and the endoscope 50 can be reinserted through the trocar sleeve 30. FIG. 9B illustrates the endoscope 50 about to be introduced into the trocar sleeve 30. Once the endoscope 50 is advanced through the trocar sleeve 30 to position the distal end of the endoscope 50 within the body cavity, e.g., the abdominal cavity 104, various medical procedures can be performed. The trocar sleeve 30 can remain in place or it can be removed leaving the endoscope 50 in place.

While not shown, the assembly can also be used in conjunction with an expandable member used to expand the size of the puncture hole to facilitate insertion of the assembly therethrough. For example, a cutting device can be used to form a puncture in the tissue, and an expandable member, such as a balloon, disposed on the cutting device or on a separate device can be advanced and positioned within the puncture. The expandable member can then be expanded to increase the size of the puncture. The endoscope can then be advanced, pushing the expanded expandable member and the endoscope through the puncture. Where this technique is used, it may not be necessary to use an obturator or end cap with the endoscope. Rather, the trocar sleeve can be positioned over the endoscope and passed through the puncture with the endoscope. The endoscope and expandable member can then be removed, leaving the trocar sleeve in place for receiving other devices therethrough.

Figure 10A:
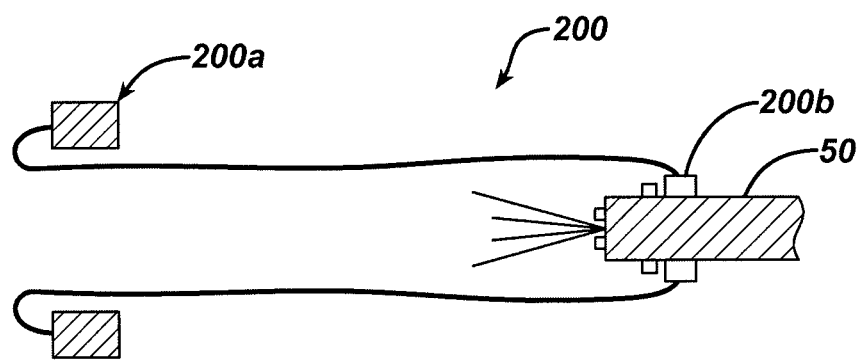
FIG. 10A is a side view of one embodiment of a protective barrier for shielding an endoscopic or laparoscopic device during insertion, showing a distal end of the barrier coupled to an endoscope.
Figure 10B:
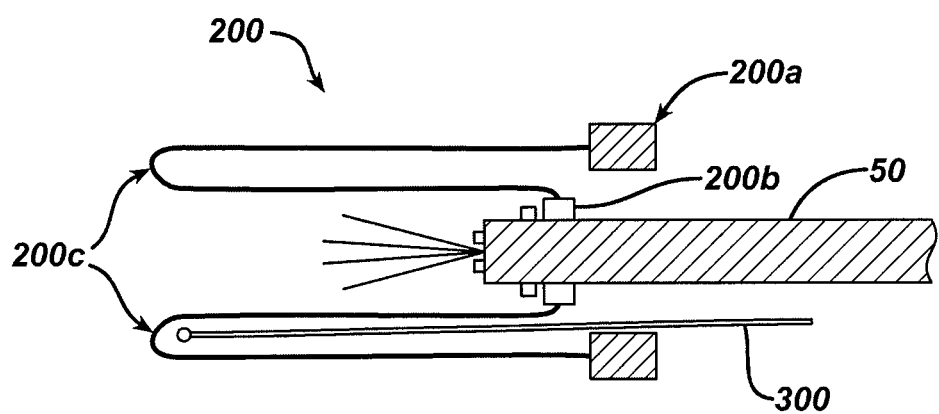
FIG. 10B is a side view of the protective barrier and endoscope of FIG. 10A showing the distal end and an endoscope inserted through the proximal end of the protective barrier.

In another embodiment, a protective barrier is provided to facilitate insertion of an endoscopic device, such as an endoscope, overtube, trocar assembly, or any other endoscopic device, through a body lumen. FIGS. 10A-10B illustrate one exemplary embodiment of a protective barrier 200 and method for using the same. The particular configuration of the barrier 200 can vary, but in an exemplary embodiment the barrier 200 has a generally elongate hollow configuration with proximal and distal ends 200a, 200b. One of the ends, e.g., the distal end 200b, can be adapted to mate or attach to a distal end of an endoscopic device, such as endoscope 50, and the other end, e.g., the proximal end 200a, can be configured to remain external to the patient or to be disposed and retained within an opening to a body lumen, such as the patient's oral cavity. The particular configuration of each end can vary. For example, the distal end 200b can be formed from a resilient material to allow the distal end 200b to be disposed over and engage an endoscope 50 or other device. The proximal end 200a can be shaped to fit within an opening of a body cavity, such as an oral cavity, or it can merely be a terminal end of the tube. In an exemplary embodiment, the proximal end 200a is flared outward to facilitate introduction of the endoscope 50 or other device and distal end 200b of the barrier 200 therethrough. In other embodiments, where the barrier 200 is formed from a resilient material, the ends 200a, 200b can merely be rolled over or folded onto themselves to form a soft terminal end surface.

At least a portion of the barrier 200 can also be formed from a flexible or resilient material to facilitate insertion of at least the flexible or resilient portion through tissue. In the embodiment shown in FIGS. 10A-10B, the entire barrier 200 is flexible to allow the mid-portion of the barrier 200 to be inserted translumenally, as will be discussed in more detail below. In other embodiments, the barrier can include a flexible or resilient portion and a portion that is more rigid. For example, the barrier can be formed using a standard overtube and a flexible sheath that is coupled to the overtube. In use, as will be discussed below, the overtube can form an inner sleeve of the device, and the flexible sheath can form an outer sleeve. The use of an overtube can provide support to the esophagus, which may be important in certain applications, such as an obese patient, prior conditions and operations, etc.

In use, as shown in FIGS. 10A-10B, a mid-portion 200c of the barrier 200 is inserted translumenally preferably through the entire length of the body lumen, such as an esophagus, while the proximal and distal ends 200a, 200b remain outside of or just within the opening to the body cavity. Various inserter tools known in the art can be used to insert the mid-portion translumenally. For example, at least one support rod 300 can be positioned between the proximal end distal ends 200a, 200b of the barrier 200 and it can be advanced into the mid-portion 200c of the barrier 200 and through a body lumen to insert the mid-portion 200c through the body lumen. As a result, the barrier 200 will include an inner sheath and an outer sheath that extend through the lumen. Where the barrier includes an overtube or other more rigid portion, the flexible portion can form the outer sleeve, and the overtube can form the inner sleeve. Alternatively, the flexible portion can have a length that allows the flexible portion to form both the inner and outer sleeves, and the overtube can remain outside the body.

The distal end 200b of the barrier 200 can be coupled to an endoscopic device, such as endoscope 50, and once the mid-portion 200c is inserted through the body lumen, the endoscope 50, with the distal end 200b of the barrier 200 attached thereto, can be inserted into the proximal end 200a of the barrier 200 and through the body lumen. Again, where the barrier includes an overtube, the overtube can couple to the endoscope or other device and the overtube and endoscope can be inserted together through the flexible portion. As the endoscope 50 is being inserted through the barrier 200, the barrier 200 will prevent contact between the endoscope 50 and the body lumen, thereby shielding the endoscope 50 and preventing any bacteria within the body lumen from being brought into a body cavity, such as the stomach. In an exemplary embodiment, the barrier 200 preferably has a length that allows the barrier 200 to extend through the entire body lumen, such as the esophagus, and into, for example, the stomach so there is no contact between the endoscope and the esophagus. Once the endoscope 50 is positioned in the stomach or other body lumen, various other procedures, such as those previously described, can be performed. For example, an endoscopic accessory can be inserted through the endoscopic device to facilitate insertion of the endoscopic device through tissue. A person skilled in the art will appreciate that the barrier can be used in a variety of endoscopic and laparoscopic procedures, and it can have a variety of configurations to facilitate mating to and use with an endoscopic or laparoscopic device.

In another exemplary embodiment, the various devices disclosed herein, or portions thereof, can be designed to be disposed of after a single use, or they can be designed to be used multiple times. For example, after at least one use, the device can be disassembled, followed by cleaning or replacement of particular pieces, and subsequent reassembly. By way of example, the end cap disclosed herein can be provided as a kit containing multiple end caps (the sizes can be the same or they can vary). After at least one use of the device, the end cap can be removed, the endoscope can be cleaned, and a new end cap can be placed on the endoscope to prepare for subsequent use. The various other devices disclosed herein can also be disassembled after at least one use, and any number of the particular pieces can be selectively replaced or removed in any combination. Replacement of pieces can also include replacement of portions of particular elements. Upon cleaning and/or replacement of particular parts, the device can be reassembled for subsequent use either at a reconditioning facility, or by a surgical team immediately prior to a surgical procedure. Those skilled in the art will appreciate that reconditioning can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A translumenal trocar device, comprising:
   a flexible elongate sleeve having an inner lumen extending between proximal and distal ends thereof and forming a working channel for receiving and guiding instruments to a surgical site;
   a seal disposed within the inner lumen of the elongate sleeve such that instruments received in the working channel pass through the seal;
   an anti-microbial agent effective to sterilize instruments passed through the lumen to maintain a sterile surgical site, the anti-microbial agent comprising at least one of a coating located on the seal and a material at least partially forming the seal; and
   an enclosed reservoir coupled to the elongate sleeve and external to the inner lumen that is adapted to controllably deliver an anti-microbial solution to the elongate sleeve for transfer onto an instrument passed through the lumen.

2. The device of claim 1, further comprising a housing having the flexible elongate sleeve extending distally therefrom, and a second seal disposed within the housing that is adapted to form a seal around instruments passed therethrough.

3. The device of claim 1, wherein the reservoir is configured to deliver the anti-microbial solution to the seal.

4. The device of claim 1, wherein the anti-microbial agent comprises an anti-microbial coating disposed on at least a portion of the elongate sleeve.

5. The device of claim 1, further comprising an obturator removably disposable through the lumen in the elongate sleeve and having a distal end adapted to penetrate through tissue.

6. The device of claim 5, wherein the obturator includes an anti-microbial agent.

7. The device of claim 6, wherein the anti-microbial agent of the obturator comprises a coating disposed on at least a portion of the obturator.

8. The device of claim 1, wherein the reservoir is configured to controllably deliver an amount of the anti-microbial solution to the elongate sleeve in response to selective opening and closing of a valve element coupled to the reservoir.

9. The device of claim 8, wherein the valve element comprises a push-button valve.

10. A method for maintaining a sterile surgical site, comprising:
    positioning a flexible tube through a body lumen, the flexible tube defining a first inner lumen having a sponge disposed therein, and the flexible tube extending distally from a housing, the housing defining a second inner lumen having a seal contained therein; and
    inserting an instrument through the second inner lumen of the housing and subsequently through the first inner lumen of the flexible tube to position a distal end of the instrument adjacent to a treatment site, the instrument passing through the seal before passing and directly contacting the sponge, the seal forming a seal with the instrument passed therethrough, and the seal including an anti-microbial agent that sterilizes the instrument as it is passed through the flexible tube.

11. The method of claim 10, wherein positioning the flexible tube comprises positioning a distal end of the tube adjacent to tissue to be penetrated while a proximal end of the tube remains outside of a patient's body.

12. The method of claim 11, further comprising penetrating the distal end of the instrument through the tissue located adjacent to the distal end of the tube to position the distal end of the instrument within a body cavity.

13. The method of claim 12, further comprising removing the instrument from the body cavity and the flexible tube, the anti-microbial agent sterilizing the instrument as it is removed, and introducing a second instrument through the flexible tube, the anti-microbial agent sterilizing the second instrument as it passed through the flexible tube.

14. The method of claim 10, wherein the anti-microbial agent comprises a solution and the method further comprises delivering the solution to the flexible tube.

15. A translumenal trocar device, comprising:
    a housing having a first inner lumen extending therethrough;
    a flexible elongate sleeve extending distally from the housing and having a second inner lumen extending between proximal and distal ends thereof and being in communication with the first inner lumen, the first and second inner lumens forming a working channel for receiving and guiding instruments to a surgical site;
    a seal disposed within the second inner lumen of the elongate sleeve such that instruments received in the working channel pass through the seal; and
    a sponge disposed within the second inner lumen of the elongate sleeve such that instruments received in the working channel pass through and directly contact the sponge after passing through the seal, the sponge having an anti-microbial agent contained therein that is effective to sterilize instruments passed through the lumen to maintain a sterile surgical site.

16. A method for maintaining a sterile surgical site, comprising:
    positioning a flexible tube through a body lumen, the flexible tube having a seal and a sponge disposed therein, and the flexible tube extending distally from a housing; and
    inserting an instrument through the flexible tube to position a distal end of the instrument adjacent to a treatment site, the seal having a proximal end and a distal end, the sponge having a proximal end and a distal end, and the distal end of the seal being spaced a distance away from the proximal end of the sponge such that the instrument passes through the seal before passing through the sponge, the sponge including an anti-microbial agent that sterilizes the instrument as it is passed through the flexible tube.

17. The method of claim 16, wherein the anti-microbial agent comprises a solution that is delivered to the sponge.

* * * * *